United States Patent
Gras et al.

Patent Number: 5,719,240
Date of Patent: Feb. 17, 1998

[54] COMPOUNDS CONTAINING CYCLIC AMIDINE AND URETDIONE GROUPS, A PROCESS FOR THEIR PREPARATION AND THE USE THEREOF

[75] Inventors: Rainer Gras, Bochum; Elmar Wolf, Recklinghausen, both of Germany

[73] Assignee: Huels Aktiengesellschaft, Marl, Germany

[21] Appl. No.: 770,429

[22] Filed: Dec. 20, 1996

[30] Foreign Application Priority Data

Dec. 28, 1995 [DE] Germany .................. 195 49 029.0

[51] Int. Cl.$^6$ .................. C07D 403/14; C08G 18/79; C09J 175/04
[52] U.S. Cl. .................. 525/528; 528/45; 528/117; 548/313.1; 548/326.5; 548/334.1
[58] Field of Search .................. 525/528; 528/45, 528/117; 548/313.1, 326.5, 334.1; 540/202

[56] References Cited

U.S. PATENT DOCUMENTS

| | | | |
|---|---|---|---|
| 4,355,058 | 10/1982 | Gras et al. | 427/386 |
| 4,476,054 | 10/1984 | Disteldorf et al. | 544/222 |
| 4,496,684 | 1/1985 | O'Connor et al. | 524/591 |

FOREIGN PATENT DOCUMENTS

| | | |
|---|---|---|
| 0 191 915 | 8/1986 | European Pat. Off. . |
| 0 601 793 | 6/1994 | European Pat. Off. . |
| 2 248 776 | 4/1974 | Germany . |
| 33 28 133 | 2/1985 | Germany . |

Primary Examiner—Frederick Krass
Attorney, Agent, or Firm—Oblon, Spivak, McClelland, Maier & Neustadt, P.C.

[57] ABSTRACT

A compound containing cyclic amidine groups and uretdione groups, having the formula:

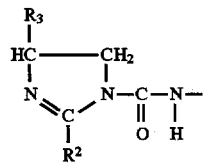

(I)

-continued

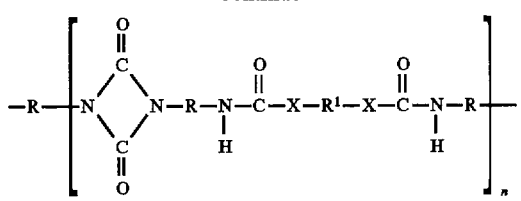

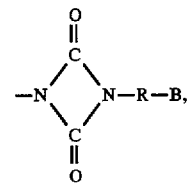

wherein X is O or NR$^2$,

R is the hydrocarbon radical of isophorone diisocyanate:

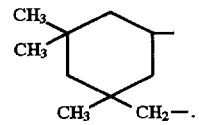

R$^1$ is a substituted (cyclo)alkylene radical which is substituted with 0–3 CH$_3$ groups and has 2–14 carbon atoms @

R$^2$ and R$^3$ are identical or different (cyclo)alkyl radicals having 1–10 carbon atoms or are phenyl radicals, n is 0–5, and B is 0–1 NCO group and/or 1–0 imidazoline-blocked NCO group of the formula:

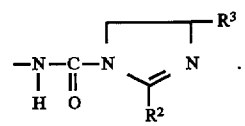

14 Claims, No Drawings

COMPOUNDS CONTAINING CYCLIC AMIDINE AND URETDIONE GROUPS, A PROCESS FOR THEIR PREPARATION AND THE USE THEREOF

BACKGROUND OF THE INVENTION

1. Field of the Invention

The present invention relates to compounds containing cyclic amidine groups and uretdione groups, to a process for their preparation and to use of the compounds.

2. Description of the Background

DE-A 36 10 758 describes EP hardeners which cure epoxy resins based on bisphenol A both by polymerization of the epoxy groups of the resins (catalytic reaction) and by reaction with the OH groups of the resins (stoichiometric reaction). Relative to the known EP powders, the EP powders produced using these hardeners are notable for outstanding solvent resistance. A disadvantage of the powders of DE-A 36 10 758, however, is that they are not suitable for bonding metals, since the metal sheets bonded therewith exhibit poor lap shear strengths (DIN 53 283) at elevated temperatures.

SUMMARY OF THE INVENTION

Accordingly, one object of the present invention is to provide a hardener for pulverulent epoxy resin powder adhesives which, when applied to metal sheets, result in improved bonding strength of the metal sheets to each other.

Briefly, this object and other objects of the present invention as hereinafter will become more readily apparent can be attained by a compound containing cyclic amidine groups and uretdione groups and having the composition:

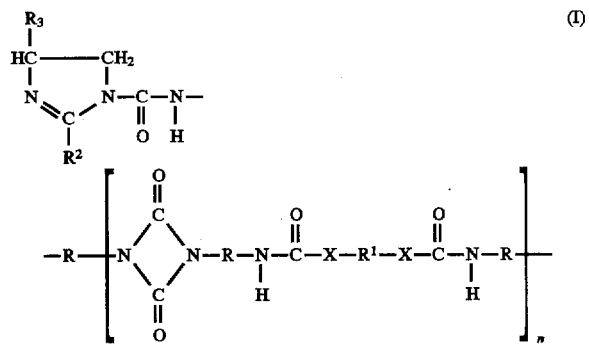

(I)

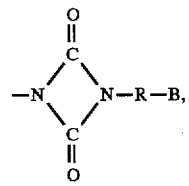

wherein X is O or $NR^2$,

R is the hydrocarbon radical of isophorone diisocyanate:

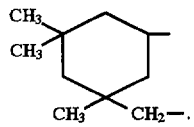

$R^1$ is a substituted (cyclo)alkylene radical which is substituted with 0–3 $CH_3$ groups and has 2–14 carbon atoms $R^2$ and $R^3$ are identical or different (cyclo)alkyl radicals having 1–10 carbon atoms or are phenyl radicals, n is 0–5, and B is 0–1 NCO group and/or 1–0 imidazoline-blocked NCO group of the formula:

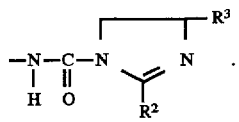

Another aspect of the invention is a process for the preparation of the compound (I) of the invention, which occurs in two stages, wherein, in the first stage, the isophorone diisocyanate uretdione (IPDI uretdione) is chain-extended with a diol or disecondary diamine by the following equation:

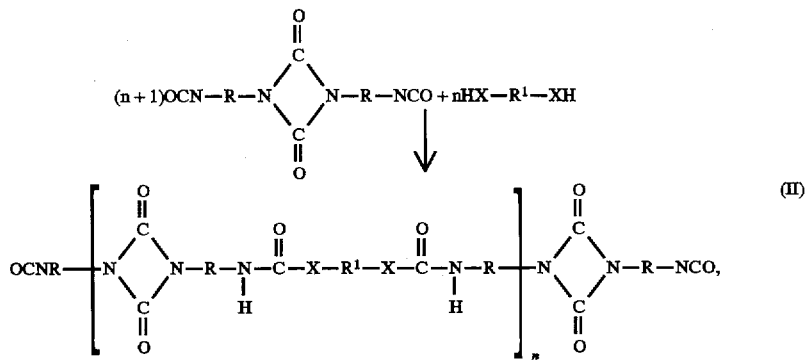

and, in the second step, the chain-extended isophorone diisocyanate uretdione (II) is partially or completely reacted with cyclic amidines of the formula:

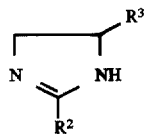

where x, R, $R^1$, $R^2$, $R^3$ and n are as defined above

DETAILED DESCRIPTION OF THE PREFERRED EMBODIMENTS

The compound of formula (I) has a uretdione group content of 1.5–2 mmol/g, a cyclic amidine group (imidazoline) content of 0.3–2% by weight, and a free NCO group content of 0.2–7% by weight, preferably 1–3% by weight. The melting point of the compound is within a range of about 80°–160° C. The present compound further is outstandingly suitable for the preparation of solvent-resistant epoxy resin powder coatings and for bonding metals with enhanced lap shear strength at elevated temperatures.

The IPDI uretdione employed in the process according to the invention is described in DE-A 30 30 513 and has an NCO content of 17–18% by weight with a monomer content of <0.7% by weight, after heating at 180° C. (0.5 h) the NCO content is 37–37.6% by weight.

The reaction between IPDI uretdione and diol or disecondary diamine is carried out in an inert solvent, for example, an aromatic hydrocarbon, an ester or a ketone. Acetone has proven to be a particularly advantageous solvent.

The compounds which are suitable for the chain extension of the IPDI uretdione are, on the one hand, diols as described, for example, in DE-A 27 38 270, p. 10, and on the other hand disecondary diamines, as are obtained, for example, in a known manner from the corresponding diprimary diamines by reaction with a carbonyl compound, for example a ketone or aldehyde, followed by hydrogenation. A particularly simple method of preparing the disecondary compounds is the addition reaction of acrylic esters ($CH_2$=CH—$COOR^2$) with the primary amino groups of the diprimary diamines ($H_2N$—$R^1$—$NH_2$).

In the chain extension of the IPDI uretdione with diols, the diol, for example ethylene glycol, diethylene glycol, butanediol, 3-methyl-1,5-pentanediol, 1,6-hexanediol, decanediol, dodcanediol or 2,2,4(2,4,4)-trimethyl-1,6-hexanediol, is added at 60° C. to the acetone solution of the IPDI uretdione and the mixture is heated further at 60° C. until one NCO group is reacted per OH group employed. In order to accelerate the reaction it has proven advantageous to add 0.01–0.1% by weight of dibutyltin dilaurate (DBTL). In reacting the IPDI uretdione with disecondary diamines, the diamine is metered at room temperature into the acetone solution of IPDI uretdione at a rate such that the temperature of the reaction mixture does not exceed 40° C. After the end of the addition of diamine, the reaction too is also virtually at an end. The addition of a catalyst is not necessary.

Then, in order to prepare the compound according to the invention, the reaction product from the first stage, which is the acetone solution of the chain-extended IPDI uretdione, is reacted in a 2nd reaction step with the cyclic amidine at 60° C. The cyclic amidine is added at about 60° C. in portions to the acetone solution of the chain-extended IPDI uretdione. After the end of the addition of amidine, heating is continued for about 1 h in order to complete the reaction. Then the acetone is removed by distillation. Then a vacuum is applied in order to remove the last residues of acetone. It has been found particularly advantageous to isolate the reaction product by removing the acetone in a film extruder under vacuum.

By the process according to the invention, 1–2 mol of cyclic amidine are reacted per mol of chain-extended IPDI uretdione ($\lambda 2$ NCO equivalents). The cyclic amidines which are appropriate for preparing the compounds according to the invention are described in DE-A 22 48 776 and DE-A 28 35 029. Particularly suitable amidines are 2-phenylimidazoline, 2-phenyl-4-methyl-imidazoline and 2,4-dimethylimidazoline.

The present invention also provides pulverulent coating compositions of high storage stability and excellent solvent resistance which are based on 1,2-epoxide compounds having more than one 1,2-epoxide group and more than one OH group in the molecule, on curing agents and on customary coatings additives, wherein the coating composition comprises the following compound as a hardener:

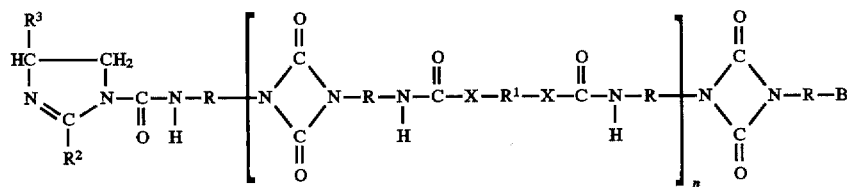

in which X, R, $R^1$, $R^2$, $R^3$, n and B are as defined supra, having an OH:NCO ratio of from 1:0.25 to 1:1, preferably 1:0.5, the content of cyclic amidine (in bonded form) is from 2 to 8% by weight, preferably from 3 to 6% by weight, based on the sum of epoxide compound and hardener, and the hardener comprises from 0.5 to 1 mol of cyclic amidine per NCO equivalent.

The hardener (1) according to the invention is compatible with OH-containing EP resins and at elevated temperatures produces homogeneous melts which are very suitable for preparing pulverulent coating compositions. They are stable on storage at room temperature, with curing times within 30–5 minutes in the temperature range 160°–200° C.

Epoxide compounds which are suitable for preparing the pulverulent coating compositions according to the invention, which are to be used as powder coatings, are of course only those containing more than one OH group in the molecule. These are EP resins which are obtained by reacting bisphenol A and epichlorohydrin in a molar ratio of n:(n+1) where n is 2–7. Particularly suitable epoxy resins are those having a EP equivalent weight of about 900 and an OH equivalent weight of 300.

The powder coatings are prepared, for example, by grinding and mixing the individual components, which are EP resin, chain-extended IPDI uretdione blocked with cyclic amidines, and, if desired, additives such as levelling agents, pigments, fillers, UV stabilizers and antioxidants and extruding the mixture at 80°–110° C., preferably 90°–100° C. After extrusion, the mass is cooled and is ground to a particle size of less than 100 µm. In the preparation of the binder mixture, the components must be matched to each other such that per OH equivalent of the EP resin there is 0.25–1, preferably 0.5, blocked NCO group of the hardener together with a cyclic amidine content (in blocked form) of 2–8% by weight, preferably 3–6% by weight, based on the sum of resin +hardener. The proportion of hardener, therefore, must be chosen such that its cyclic amidine content is sufficient for catalytic curing of the EP resin (polymerization of the epoxide groups) without the OH groups reacting, and at the same time achieving crosslinking of the EP resin by reaction of the OH groups of the EP resin with the blocked NCO groups of the hardener, the EP groups, however, remaining intact.

The application of the powder coatings to the substrates to be coated can be carried out by known methods, for example by electrostatic powder spraying or fluidized-bed sintering. The coated articles are subsequently cured for 5–30 minutes in the temperature range 200°–160° C. Substrates suitable for coating with the pulverulent coating compositions according to the invention are all those which withstand the curing conditions indicated, examples being metals, glass and ceramic. The powder coatings thus prepared are notable for very good coatings properties and outstanding resistance to aggressive solvents such as, for example, methyl isobutyl ketone.

The present invention also embodies the use of the compounds of the invention in the preparation of pulverulent, one-component metal adhesives.

The resin/hardener mixture suitable for bonding metals is identical with the pulverulent coating compositions, i.e. has the same composition, preparation and application, and in the case of the bonding of metals it is even sufficient to apply the powder to the metal panels by sieving. After the clean surface of one metal has been coated with the resin/hardener mixture according to the invention, it is fixed with the other metal to be bonded with the aid of a screw clamp. Curing takes place, as in the case of the powder-coated substrates, at 160°–200° C. within 30–5 minutes.

The metal bonds thus produced differ markedly from the EP-based one component metal adhesives currently available on the market with respect to their strength (lap shear strength as determined by the procedure of DIN 53 283) at elevated temperatures.

The pulverulent metal adhesives based on EP resins that are currently on the market consist of a (solid) EP resin which is cured with dicyandiamide. The metal bonds produced therewith exhibit lap shear strengths which are excellent at room temperature but which decrease sharply with rising temperature and are virtually zero at 150° C., in other words, the bond fails at 150° C., whereas bonds with the resin/hardener mixture according to the invention still have lap shear strengths at 150° C. which are about 10 N/mm².

A) A Method of Preparation of the Compound of the Invention

The diol is metered in over the course of about 1 hour with intensive stirring to an acetone solution of the IPDI uretdione (about 50% acetone based on the sum of IPDI uretdione+chain extender+cyclic amidine), which contains 0.05% by weight dibutyltin dilaurate, and the mixture is heated further at 60° C. until one NCO equivalent has reacted per OH equivalent employed. The cyclic amidine is then added in portions. After the addition of amidine has taken place, heating is continued at 60° C. for about 1 h .

The acetone is then removed by distillation. In order to remove the last residues of acetone, vacuum is applied to the reaction mass. If a disecondary diamine is used instead of the diol for chain extension of the IPDI uretdione, the reaction takes place at room temperature and without DBTL.

The IPDI uretdione used for chain extension was prepared in accordance with the reaction conditions described in Example 2 of DE-A 30 30 513. The NCO content of the IPDI uretdione was 17.3%; on heating at 180° C. (0.5 h) an NCO content of 37% was found.

TABLE 1

Compounds according to the invention

| Example No. | IPDI Uretdione [mol] | Chain extender [mol] | Cyclic amine [mol] | m.p. [°C.] | Glass transition point (DSC) [°C.] | % NCO (free) | % NCO (after heating at 180° C. for 1 h) | NH₂ [mmol/g] |
|---|---|---|---|---|---|---|---|---|
| A) 1 | 1 | — | 1 HN (B 31) | 66–75 | 35–48/42 | 6.6 | 28.4 | 1.6 |
| A) 2 | 3 | 2 HO—(CH₂)₆—OH | 2 B 31 | 127–135 | 96–112/100 | 0.1 | 18.7 | 1.0 |
| A) 3 | 2 | 1 HO—(CH₂)₆—OH | 2 B 31 | 123–130 | 88–112/93 | 0.2 | 19.8 | 1.4 |
| A) 4 | 3 | 2 HO—(CH₂)₁₂—OH | 2 B 31 | 116–127 | 80–98/84 | 0.1 | 17.2 | 0.9 |
| A) 5 | 2 | 1 HO—(CH₂)₁₂—OH | 2 B 31 | 111–122 | 79–98/82 | 0.1 | 18.8 | 1.3 |
| A) 6 | 4 | 3 HO—CH₂—CH₂—OH (EG) | 2 B 31 | 146–153 | 123–134/126 | <0.1 | 19.3 | 0.8 |
| A) 7 | 3 | 2 EG | 2 B 31 | 133–141 | 117–128/122 | <0.1 | 19.7 | 1.06 |
| A) 8 | 2 | 1 EG | 2 B 31 | 128–139 | 108–118/115 | <0.1 | 20.7 | 1.5 |

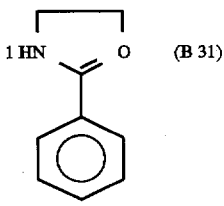

TABLE 1-continued

Compounds according to the invention

| | Composition of the compounds according to the invention | | | | Glass transition point (DSC) [°C.] | % NCO (free) | % NCO (after heating at 180° C. for 1 h) | NH$_2$ [mmol/g] |
|---|---|---|---|---|---|---|---|---|
| Example No. | IPDI Uretdione [mol] | Chain extender [mol] | Cyclic amine [mol] | m.p. [°C.] | | | | |
| A) 9 | 5 | 4 HN—R*)—NH<br>    \|        \|<br>  C$_4$H$_9$  C$_4$H$_9$ | 1 HN⟨ ⟩N—CH$_3$ / CH$_3$ | 163–175 | 132–145/140 | 1.2 | 15.4 | 0.3 |

*)R = HC radical of isophoronediamine

B) Epoxy Resin Powder Coatings General Preparation Procedure

The ground products each of hardener, epoxy resin and levelling agent masterbatch, were first of all mixed in dry form with the white pigment in an edge runner mill and then homogenized in an extruder at 80°–120° C. After cooling, the extrudate was crushed and ground in a pinned-disk mill to a particle size of <100 μm. The powder thus produced was applied with an electrostatic powder spraying unit at 60 kV to degreased, optionally pretreated iron panels (1 mm thick) and baked in a laboratory convection oven.

Leveling Agent Masterbatch

10% by weight of the levelling agent, which is a commercially available acrylate-oligomer, are homogenized in the melt in the epoxy resin and, after solidifying, are comminuted.

Epoxy Resin

In the epoxy resin coating examples infra, a solid epoxy resin was used of the diglycidyl ether of bisphenol A prepared by reacting epichlorohydrin with bisphenol A, which, according to the manufacturer, has an epoxide equivalent weight of 900–1000, an epoxide value of 0.10–0.11, a hydroxyl value of 0.34 and a melting point of 96°–104° C.

Composition of the EP Powder

The powder coatings listed in Table 2 contain 40 parts by weight of TiO$_2$, 0–5 part by weight of levelling agent, 59.5 parts by weight of binder, with the OH:NCO equivalence ratio of resin to hardener being generally 2:1.

The abbreviations in the tables below have the following meanings

CD: Coat thickness in μm

HK: König hardness in sec (DIN 53 157)

EI: Erichsen indentation in mm (DIN 53 156)

GG 60° ⋖: Gardner gloss (ASTM-D 523)

Imp. rev.:Impact reverse in g·m

CH: Cross-hatch test (DIN 53 151)

MEK (methyl ethyl ketone) resistance:

Number of strokes with an MEK-soaked cottonwool pad under a load of 1 kg until the surface is attacked (matt surface).

TABLE 2

Composition of the pigmented (40% by weight TiO$_2$) powders and the coatings data (after curing)

| | | | | | Temp. [°C.] | | | | | |
|---|---|---|---|---|---|---|---|---|---|---|
| | NCO | OH | | | 200 | | | 180 | | 170 |
| Example No. | equiv. hardener | equiv. EP | | | Duration [min] | | | | | |
| | | | | | 10 | 20 | 30 | 15 | 25 | 25 | 30 |
| B) 1 | 1 A) 2 | 2 | HK | | 138 | 150 | 140 | 154 | 152 | 155 | 153 |
| | | | GG 60°⋖ | | 29 | 29 | 30 | 26 | 26 | 25 | 28 |
| | | | CH | | 0 | 0 | 1 | 0 | 0 | 1 | 0 |
| | | | EI | | 3.1 | 3.4 | 6 | 1 | 1.3 | 1.8 | 1.3 |
| | | | BI rev. | | 20 | 10 | <10 | <10 | <10 | <10 | <10 |
| | | | MEK | | 120 | 180 | 200 | >200 | >200 | 200 | 200 |
| B) 2 | 1 A) 3 | 2 | HK | | 147 | 153 | 154 | 155 | 168 | 163 | 158 |
| | | | GG 60°⋖ | | 40 | 53 | 56 | 42 | 44 | 38 | 45 |
| | | | CH | | 1 | 1 | 0 | 1 | 1 | 1 | 1 |
| | | | EI | | 4.5 | 3.8 | 4.1 | 1.8 | 1.8 | 2.6 | 2.8 |
| | | | BI rev. | | 20 | 10 | 10 | <10 | <10 | <10 | <10 |
| | | | MEK | | >200 | >200 | >200 | >200 | >200 | >200 | >200 |
| B) 3 | 1 A) 4 | 2 | HK | | 185 | 183 | 175 | 192 | 184 | 179 | 180 |
| | | | GG 60°⋖ | | 78 | 82 | 84 | 85 | 83 | 78 | 88 |
| | | | CH | | 1 | 1 | 1 | 1 | 1 | 0 | 0 |
| | | | EI | | 7 | 7.8 | 7.4 | 6.7 | 6.4 | 7.1 | 6.7 |
| | | | BI rev. | | 60 | 50 | 50 | 50 | 50 | 40 | 40 |
| | | | MEK | | >200 | >200 | >200 | >200 | >200 | 150 | 180 |
| B) 4 | 1 A) 5 | 2 | HK | | 164 | 169 | 169 | 180 | 177 | 170 | 170 |

TABLE 2-continued

Composition of the pigmented (40% by weight TiO₂) powders and the coatings data (after curing)

| Example No. | NCO equiv. hardener | OH equiv. EP | | Temp. [°C.] | | | | | | |
|---|---|---|---|---|---|---|---|---|---|---|
| | | | | 200 | | | 180 | | 170 | |
| | | | | Duration [min] | | | | | | |
| | | | | 10 | 20 | 30 | 15 | 25 | 25 | 30 |
| | | | GG 60°✗ | 80 | 76 | 68 | 68 | 69 | 60 | 70 |
| | | | CH | 4 | 3 | 3 | 0 | 0 | 0 | 0 |
| | | | El | 4.5 | 4.3 | 4.5 | 4.5 | 3.1 | 5.1 | 5.2 |
| | | | Bl rev. | 30 | 20 | 20 | <10 | <10 | <10 | <10 |
| | | | MEK | 80 | 120 | 200 | 130 | 180 | 80 | 110 |
| B) 5 | 1 A) 6 | 2 | HK | 101 | 130 | 109 | 133 | 140 | 139 | 128 |
| | | | GG 60°✗ | 11 | 10 | 11 | 13 | 12 | 12 | 12 |
| | | | CH | 0 | 0 | 0 | 0 | 0 | 0 | 0 |
| | | | El | 1.1 | 1 | 0.8 | 0.9 | 0.8 | 0.6 | 0.7 |
| | | | Bl rev. | <10 | <10 | <10 | <10 | <10 | <10 | <10 |
| | | | MEK | 200 | 200 | 200 | 16 | 40 | 20 | 26 |
| B) 6 | 1 A) 7 | 2 | HK | 117 | 110 | 116 | 153 | 141 | 137 | 136 |
| | | | GG 60°✗ | 19 | 18 | 19 | 21 | 20 | 20 | 21 |
| | | | CH | 1 | 0 | 0 | 0 | 0 | 0 | 0 |
| | | | El | 1.1 | 1.0 | 1.4 | 0.9 | 0.9 | 0.9 | 1 |
| | | | Bl rev. | <10 | <10 | <10 | <10 | <10 | <10 | <10 |
| | | | MEK | 200 | >200 | >200 | 26 | 80 | 46 | 60 |
| B) 7a | 1 A) 1 | 2 | HK | 179 | 183 | 186 | 175 | 174 | 179 | 183 |
| | | | GG 60°✗ | 68 | 69 | 70 | 62 | 61 | 60 | 62 |
| | | | CH | 0 | 0 | 0 | 0 | 1 | 0 | 0 |
| | | | El | 2.5 | 3.0 | 3.1 | 3 | 4 | 2.8 | 3 |
| | | | Bl rev. | <10 | <10 | <10 | <10 | <10 | <10 | <10 |
| | | | MEK | >200 | >200 | >200 | >200 | >200 | >200 | >200 |
| B) 7b | 1 A) 1 | 4 | HK | 151 | 151 | 151 | 150 | 146 | 170 | 159 |
| | | | GG 60°✗ | 30 | 32 | 32 | 25 | 20 | 60 | 25 |
| | | | CH | 0 | 0 | 0 | 0 | 0 | 0 | 0 |
| | | | El | 3.3 | 4.2 | 3.8 | 3 | 3.5 | 5.1 | 2 |
| | | | Bl rev. | <10 | <10 | <10 | <10 | <10 | <10 | <10 |
| | | | MEK | 90 | 100 | 110 | 80 | 100 | 80 | 30 |

C) Use of the Compounds of the Invention for the Preparation of Pulverulent One-Component Adhesives The hardener of the invention and an EP resin with an EP value of 0.1 are subjected to intensive kneading in a plastograph for 5 minutes at 100° C. After cooling, the product is ground and applied by sieving to steel panels (1.5 mm thick) cleaned with Scotch-Brite, and bonding is conducted in accordance with the procedure of DIN 53 283. The lap shear strengths of these steel bonds (after curing at 200° or 180° C.) are listed in the table infra.

TABLE 3

Metal bonds (DIN 53 283) with the hardener/EP mixtures according to the invention

| | Adhesive composition | | Curing | | Lap shear strength (DIN 53 283) [N/mm²] | | | |
|---|---|---|---|---|---|---|---|---|
| Example No. | NCO equiv. Hardener | OH equiv. EP | Temperature [°C.] | Time [min] | Room temperature | 100° C. | 130° C. | 150° C. |
| C) 1 | 1 A) 7 | 2 | 180 | 30 | 20 | 16 | 10 | 9 |
| C) 2 | 1 A) 7 | 1 | 180 | 30 | 21 | 19 | 9 | 9 |
| C) 3 | 1 A) 8 | 2 | 180 | 30 | 20 | 17 | 8 | 7 |
| C) 4 | 1 A) 8 | 1 | 180 | 30 | 18 | 19 | 16 | 15 |
| C) 5 | 1 A) 4 | 2 | 180 | 30 | 21 | 19 | 7 | 6 |
| | | | 200 | 15 | 20 | 18 | 9 | 7 |
| C) 6 | 1 A) 4 | 1 | 180 | 30 | 17 | 13 | 13 | 12 |
| | | | 200 | 15 | 18 | 14 | 14 | 15 |
| C) 7 | 1 A) 5 | 2 | 180 | 30 | 21 | 18 | 17 | 14 |
| | | | 200 | 15 | 20 | 18 | 16 | 16 |
| Comparison Example | | | | | | | | |
| AT 1 (Ciba) | | | 200 | 30 | 29 | 14 | 3 | 1 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A compound containing cyclic amidine groups and uretdione groups, having the formula:

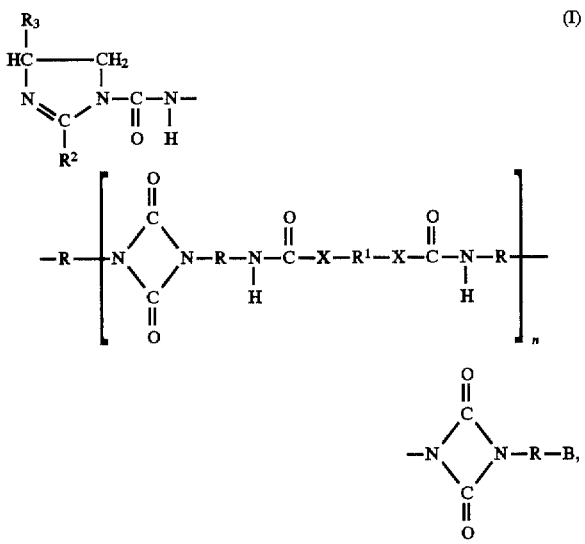

(I)

wherein X is O or $NR^2$,

R is the hydrocarbon radical of isophorone diisocyanate:

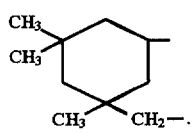

$R^1$ is a substituted (cyclo)alkylene radical which is substituted with 0-3 $CH_3$ groups and has 2-14 carbon atoms, $R^2$ and $R^3$ are identical or different (cyclo)alkyl radicals having 1-10 carbon atoms or are phenyl radicals, n is 0–5, and B is a NCO group and/or an imidazoline-blocked NCO group of the formula:

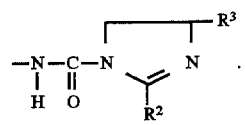

2. The compound as claimed in claim 1, which comprises radicals of 2-phenylimidazoline, 2-phenyl-4-methylimidazoline or 2,4-dimethylimidazoline.

3. The compound as claimed in claim 1, wherein the IPDI uretdione has an NCO content of 17–18% by wt.

4. The compound as claimed in claim 1, which has a uretdione group content of 1.5–2 mmole/g, a cyclic amidine content of 0.3–2% by wt. and a free NCO content of 0.2–7% by wt.

5. A process for the preparation of a compound as claimed in claim 1, which comprises, in a 1st stage, reacting isophorone diisocyanate uretdione with diols or disecondary diamines as described by the following equation:

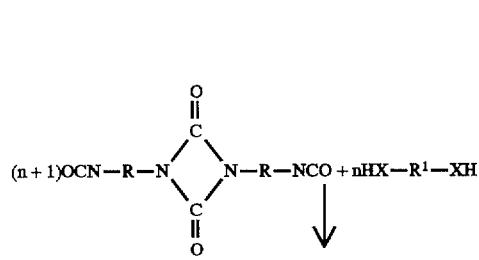

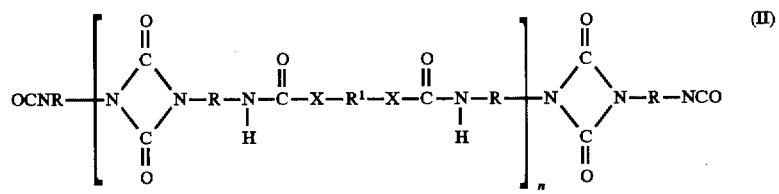

(II)

in an inert solvent; and, in the 2nd stage, reacting the chain-extended isophorone diisocyanate uretdione (II) partially or completely with a cyclic amidine(s) of the formula:

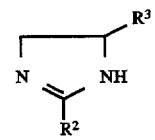

wherein x, R, $R^1$, $R^2$, $R^3$ and n are as defined in claim 1.

6. The process as claimed in claim 5, wherein acetone is employed as solvent.

7. The process as claimed in claim 5, wherein said diol is ethylene glycol, diethylene glycol, butanediol, 3-methyl-1, 5-pentanediol, 1,6-hexanediol, decanediol, dodecanediol or 2,2,4 (2,4,4)-trimethyl-1,6-hexanediol.

8. The process as claimed in claim 5, wherein dibutyl-tin dilaurate is added to said first stage reaction in an amount of 0.01–0.1% by wt.

9. A pulverulent coating composition, which comprises:

(1) a 1,2-epoxide compound(s) having more than one 1,2-epoxide group and more than one OH group in the molecule, (2) an epoxide curing agent excluding hardener (4), (3) coating additives, and (4) a hardener(s) of the formula:

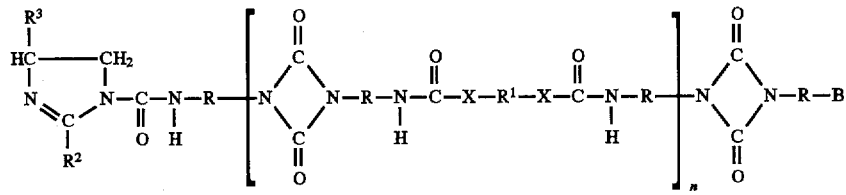

wherein X is O or $NR^2$,

R is the hydrocarbon radical of isophorone diisocyanate:

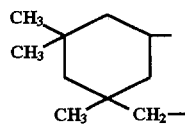

$R^1$ is a substituted (cyclo)alkylene radical which is substituted with 0–3 $CH_3$ groups and has 2–14 carbon atoms, $R^2$ and $R^3$ are identical or different (cyclo)alkyl radicals having 1–10 carbon atoms or are phenyl radicals, n is 0–5, and B is a NCO group and/or a imidazoline-blocked NCO group of the formula:

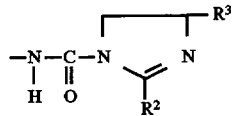

the content of cyclic amidine (in bonded form) being from 2 to 8% by weight based on the sum of epoxide compound and hardener (4), the hardener comprising from 0.5 to 1 mol of cyclic amidine per NCO equivalent and, per OH equivalent of the epoxide compound there are 0.25 to 1 blocked NCO groups in hardener (4).

10. The pulverulent coating composition of claim 9, wherein the content of cyclic amidine ranges from 3–6% by weight based on the sum of epoxide compound hardener (4).

11. The pulverulent coating composition as claimed in claim 9, wherein the OH:NCO ratio is 1:0.5.

12. The pulverulent coating composition as claimed in claim 9, wherein the content of cyclic amidine is from 3 to 6% by weight and the OH:NCO ratio is 1:0.5.

13. The pulverulent coating composition of claim 9, wherein said epoxy resin has an epoxide equivalent weight of about 900 and an OH equivalent weight of 300.

14. A one-component pulverulent adhesive, comprising the pulverulent composition of claim 9.

* * * * *